United States Patent [19] [11] Patent Number: 5,946,727
Wright et al. [45] Date of Patent: Sep. 7, 1999

[54] TOUCH ENHANCING MITT

[75] Inventors: Grant A. Wright; Brad E. Wright, both of Decatur, Ill.

[73] Assignee: Inventive Products, Inc., Decatur, Ill.

[21] Appl. No.: 09/134,260

[22] Filed: Aug. 14, 1998

[51] Int. Cl.⁶ ............................................. A41D 19/00
[52] U.S. Cl. ................................ 2/161.7; 2/164; 2/168; 128/95.1; 128/112.1
[58] Field of Search ............................ 2/20, 158, 161.3, 2/161.7, 161.8, 168; 128/112.1, 95.1

[56] References Cited

U.S. PATENT DOCUMENTS

| | | | |
|---|---|---|---|
| 2,695,999 | 12/1954 | Arnold | 2/20 |
| 2,976,540 | 3/1961 | Sutherland | 2/161.7 |
| 3,608,708 | 9/1971 | Storandt | 2/158 |
| 4,185,330 | 1/1980 | Stager | 2/167 |
| 4,657,021 | 4/1987 | Perry et al. | 2/168 |
| 4,793,354 | 12/1988 | Wright et al. | 434/113 |
| 5,636,406 | 6/1997 | Strong | 2/20 |
| 5,774,889 | 7/1998 | Gochanour | 2/161.7 |
| 5,799,331 | 9/1998 | Stewart | 2/158 |

*Primary Examiner*—Diana L. Oleksa
*Assistant Examiner*—Katherine Moran
*Attorney, Agent, or Firm*—Philip L. Bateman

[57] ABSTRACT

A mitt enhances the sense of touch when worn on a hand of a user as an object is touched with the palm side of the fingertips. The apparatus is formed of an enclosure of first and second layer of a pliable and elastic material, a lubricant, and a third layer of sheet material. The first and second layers are sealed together along their perimeter to form the enclosure. The lubricant inside the enclosure is present in a quantity and with sufficient lubricity that the coefficient of kinetic friction between the walls of the enclosure is less than the coefficient of kinetic friction between the fingertips and the enclosure and less than the coefficient of kinetic friction between the object being touched and the enclosure. The third layer covers part or all of the second layer and is attached to the second layer along part or all of the second layer's perimeter to form an opening between the second and third layers and to form a pocket into which the hand of the user can be inserted with the palm facing toward the second layer.

11 Claims, 2 Drawing Sheets

TOUCH ENHANCING MITT

FIELD OF THE INVENTION

This invention relates to an apparatus that enhances the sense of touch when worn on the hand as an object is touched with the fingertips of the user.

BACKGROUND OF THE INVENTION

The sense of touch is one of the five senses by which we gather information about the world around us. The sense of touch gives rise to feelings of pleasure and pain and is used to determine the shape, hardness, texture, and temperature of objects. The sense of touch is used extensively in the field of medicine because the shape and hardness of body internals is often an excellent guide in detecting, diagnosing, and treating disease.

One of the most publicized uses of the sense of touch in medical diagnosis is the detection of breast cancer. One out of every nine women in the United States develops breast cancer. It is the most common form of cancer in women and is the chief cause of cancer deaths among women in the United States. Early detection of breast cancer is extremely important in treating the disease. Breast cancer is characterized by the formation of a lump in the breast. These lumps can be detected by X-ray radiation photography (mammograms) or by manual examination of the breasts. The known tendency of X-ray radiation to cause various types of cancers limits its use for detection. Furthermore, many women fail to receive regular mammograms. Accordingly, most breast cancers are discovered by the detection of lumps by physical examination of the breasts. Manual examination of the breasts is included by most physicians in their routine examination of adult women. To help with early detection, many medical experts also recommend monthly self-examinations for women. When conducting self-examinations in a standing or sitting position, it is recommended that one arm be raised overhead. This position distributes the breast tissue over a greater area and enables a more thorough examination to be conducted.

To reduce friction and thereby facilitate movement of the hands across the breasts, the American Cancer Society recommends that the monthly self-examinations be conducted during a bath or shower when the skin is wet and soapy. For any number of reasons, many women find it inconvenient to take the additional time for self-examination during their bath or shower. And, for obvious reasons, it is not practical to use water and/or soap as a skin lubricant for breast examination when partially clothed, e.g., at a physician's office. Creams, powders, or lotions are more suitable as friction reducers, but still are rarely used because of the mess. Therefore, most physicians and women conduct breast examinations by using their hands directly on dry skin.

Unfortunately, manual examination of the breasts does not ensure that a lump will be detected. In an article entitled "Physicians' Abilities to Detect Lumps in Silicone Breast Model" published in the Apr. 19, 1985 issue of *The Journal of the American Cancer Society*, Dr. Suzanne W. Fletcher et al. of the University of North Carolina described a study which tested the ability of 80 physicians to detect lumps of varying size, hardness, and depth in silicone breast models. The authors found that the physicians were able to detect only 44 percent of the lumps.

It is not difficult to understand why the detection results were so poor in the study. When conducting a breast cancer examination with bare hands on dry skin, the examiner must ignore the unwanted touch stimuli (the "noise"), e.g., temperature, texture, and, if a self-examination, stimuli from the breast itself, in favor of the touch stimuli (the "signal") which enable the determination of shape and hardness of an object to be made. The sense of touch is clearly an ability which can be developed with practice. For example, thousands of blind persons are able to read Braille lettering, but a person touching Braille for the first time is usually unable to distinguish the number or pattern of the protrusions. Consequently, many experts have recommended more training for physicians to better develop their senses of touch.

Enhancing the sense of touch is the subject of two U.S. patents issued to Don A. Perry and H. Earl Wright, each of which is incorporated by reference. Perry et al, U.S. Pat. No. Re. 34,353, reissued Aug. 24, 1993, discloses a touch enhancing pad and a method of using the pad to enhance the sense of touch. The pad comprises a sealed enclosure of a pliable, elastic material with a liquid lubricant inside the enclosure. The pad is placed between the fingertips and the object being touched. The bottom layer of the pad remains stationary over the object being touched while the top layer moves with the fingertips. Wright et al., U.S. Pat. No. 4,793,354, issued Dec. 27, 1988, discloses a method of enhancing the sense of touch which comprises placing two layers of a pliable, elastic material between the fingertips and the object being touched, maintaining the friction between the two layers of material less than the friction between either the top layer and the fingertips or the bottom layer and the object being touched, and then moving the fingertips over the object.

A product made in accordance with the two Perry-Wright patents is currently sold by Inventive Products, Inc. of Decatur, Ill. Sales of the product, known as the SENSOR PAD®) touch enhancing pad, were begun in the United States in 1988. The current SENSOR PAD® touch enhancing pad consists of an enclosure made of polyurethane with a silicone lubricant sealed inside and a plastic handle affixed to the enclosure. The pad is an excellent enhancer of the sense of touch. However, when used for breast self-examination while sitting or standing, the pad must be held by its handle with one hand while the other hand is used for touching. This prevents the woman conducting the self-examination from raising her arm overhead in the recommended position.

Paschal, U.S. Pat. No. 2,694,396, issued Nov. 16, 1954, discloses three embodiments of a massaging device. The third embodiment, shown in FIGS. 6–9a, includes a massaging element and a detachable, washable outer shield. The outer shield attaches to the massaging element by the means of buttons that are attached to a reinforcing strip on the massaging element. The massaging element has two sheet assemblies with an open space therebetween so that an operator's hand may be inserted between the two assemblies. Although this embodiment of the Paschal device can be used with one hand, it does not enhance the sense of touch.

Accordingly, it would be a significant improvement to provide a touch enhancing pad that can be easily used with one hand that enables a woman to conduct a breast self-examination with one arm raised overhead and that also enables a physician to more conveniently conduct a breast examination.

SUMMARY OF THE INVENTION

The general object of this invention is to provide an improved apparatus for enhancing the sense of touch. A more particular object is to provide a touch enhancing mitt that can be easily used with one hand.

I have invented a mitt that enhances the sense of touch when worn on a hand of a user as an object is touched with the palm side of the fingertips. The mitt comprises: (a) an enclosure of a first and a second layer of a pliable and elastic hand-sized sheet material, the first and second layers of materials being sealed together along their perimeter to form the enclosure, the first and second layers having a wall thickness of about 0.002 to 0.020 inches, a modulus of elasticity at 200 percent elongation of less than about 5,000 psi, a tensile strength of greater than about 1,000 psi, and an ultimate elongation of greater than about 200 percent so that the enclosure is resistant to tearing or puncturing and is adapted to conform to the contours of the object being touched and to readily transmit touch stimuli; (b) a lubricant inside the enclosure in a quantity and with sufficient lubricity that the coefficient of kinetic friction between the walls of the enclosure is less than the coefficient of kinetic friction between the fingertips and the enclosure and less than the coefficient of kinetic friction between the object being touched and the enclosure; and (c) a third layer of sheet material covering part or all of the second layer and attached to the second layer along part or all of the second layer's perimeter to form an opening between the second and third layers and to form a pocket into which the hand of the user can be inserted with the palm facing toward the second layer.

The use of this mitt improves the sense of touch and is useful in many applications where the sense of touch is employed for medical diagnosis. The mitt is especially convenient because it can be used with one hand. The mitt is non-toxic, non-invasive, reusable, and leaves no residue on the hands of the user or on the object being touched.

DETAILED DESCRIPTION OF THE INVENTION

1. The Invention In General

Figure 1:
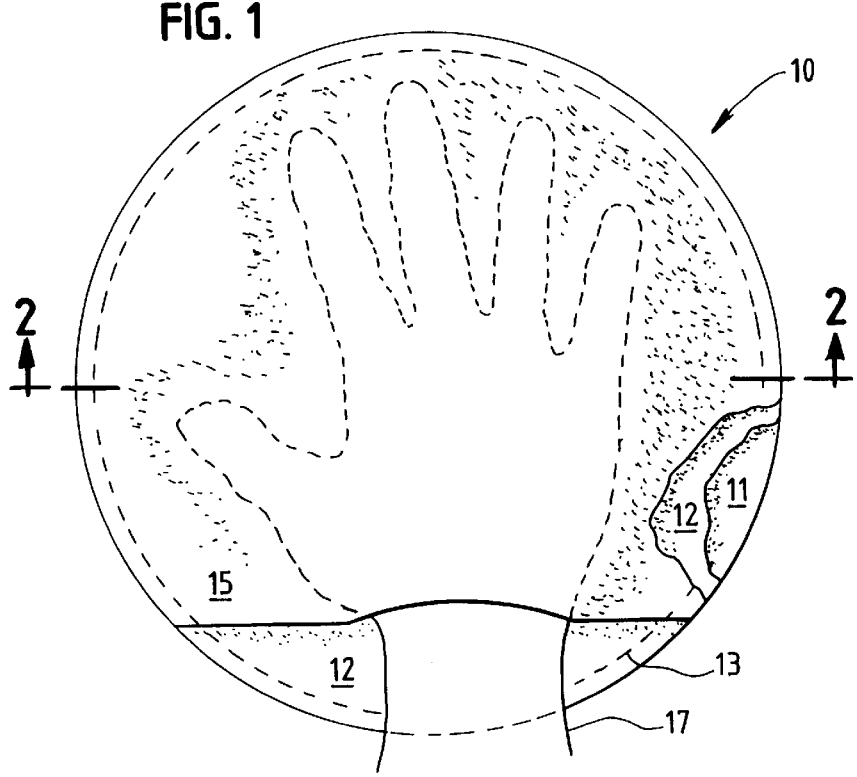
FIG. 1 is a perspective view of the preferred embodiment of the touch enhancing mitt of this invention.
Figure 2:
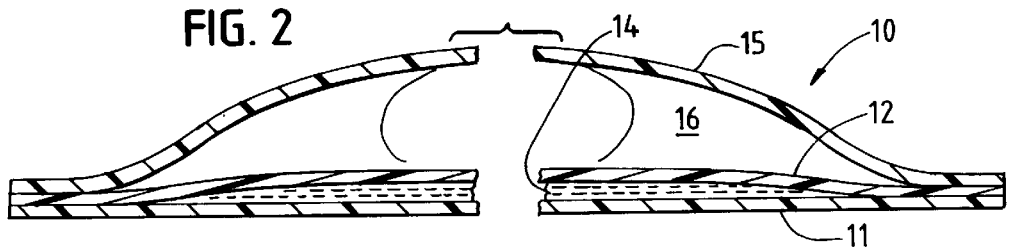
FIG. 2 is a cross-sectional view of the embodiment shown in FIG. 1 taken along the line 2—2.

This invention is best understood by reference to the drawings. The preferred embodiment of a touch enhancing mitt 10 is shown in FIGS. 1 and 2. The mitt is formed of two layers of material, a first layer 11 and a second layer 12, that are sealed together along their circumferences as represented by dotted line 13 to form an enclosure. A quantity of liquid lubricant 14 is contained between the two layers within the enclosure. A third layer of material 15 is attached to, and covers part or all of, the second layer so as to form a pocket opening 16 into which the hand of the user can be inserted. A hand 17 is shown in phantom lines in FIG. 1. The third layer of material is sealed to the second layer. To use the mitt, the hand is placed into the pocket with the palm facing the first and second layers. The mitt is then placed onto the body part, or other object, to be touched. The fingertips are then used to examine the body part just as if the mitt were not present. The first layer of the mitt (the one in contact with the body part being touched) remains stationary while the second layer (the one in contact with the fingertips) moves with the fingertips. For what is believed to be a number of reasons, the touch stimuli used to determine shape and hardness are enhanced when the mitt is used in this fashion.

2. Touch Enhancing Layers

The touch enhancing enclosure is made of a material which readily transmits the desired touch stimuli through two of its layers and yet is strong enough to resist tearing or puncturing. The ability of a material to transmit touch stimuli is believed to be primarily a function of its thickness and its ability to conform to the contours of the object being touched. This ability to conform is, in turn, primarily a function of the material's pliability, elasticity, and smoothness. In summary, the properties desired for the enclosure material are strength, thinness, pliability, elasticity, and smoothness.

The material has a tensile strength of greater than about 1,000 psi, preferably greater than about 2,000 psi, and most preferably greater than about 3,000 psi. The material has a thickness of about 0.002 to 0.020 inches, preferably about 0.005 to 0.015 inches. At this tensile strength and thickness, the material is strong enough to resist tearing or puncturing and yet thin enough to readily transmit touch stimuli. The pliability of a material can be measured in terms of its modulus of elasticity. Modulus of elasticity is the force required to stretch a material a given amount. For use in this invention, a material has a modulus of elasticity at 200 percent elongation of less than about 5,000 psi, preferably less than about 4,000 psi, and most preferably less than about 3,000 psi.

The material has sufficient elasticity so that it can be stretched to at least three times its length without breaking. In other words, the material has an ultimate elongation of greater than 200 percent. It is preferred that the ultimate elongation exceed about 300 percent and most preferred that the ultimate elongation exceed about 400 percent. The material has a uniformly smooth surface on each side so that small protrusions, such as those present in a woven material, do not interfere with the sense of touch and so that low-friction movement of one layer across the other layer is facilitated.

Materials exhibiting the above-described properties of strength, pliability, elasticity, and smoothness are generally members of the class of polymers known as elastomers. Both synthetic and natural elastomers are suitable. Representative synthetic elastomers include certain polyolefins, polychloroprene polymers, butadiene-styrene copolymers, butadiene-acrylonitrile copolymers, and polyurethane polymers. A preferred polyolefin is low density polyethylene. A highly preferred low density polyethylene is XMAX-133, a commercial product of CT Films, Chippewa Falls, Wis. This polyethylene has a modulus of elasticity at 300 percent of about 1900 psi, a tensile strength of about 3700 psi, and an ultimate elongation of about 1100 percent. A suitable polyurethane polymer is Type TF-840 polyurethane film, a commercial product of the Lord Corporation, Erie, Pa. A highly preferred polyurethane polymer is PELLETHANE 2103-80PF polyurethane, a commercial product of the Dow Chemical Company, Midland, Mich. This particular polyurethane exhibits a modulus of elasticity at 300 percent of about 2,500 psi, a tensile strength of about 8,000 psi, and an ultimate elongation of about 650 percent. A preferred natural elastomer is natural rubber latex derived from the tree Hevea Braziliensis. Natural rubber latex generally exhibits superior properties of strength, pliability, and elasticity. For example, natural rubber latex often exhibits a modulus of elasticity at 300 percent of less than 700 psi, a tensile strength of greater than 4,000 psi, and an ultimate elongation of greater than about 700 percent.

3. Lubricating Means

The preferred embodiment of the mitt contains a liquid lubricant between the first and second layers of material within the enclosure. The lubricant is present in a quantity and has sufficient lubricity so that the top layer moves with the fingertips while the bottom layer remains stationary over the body part being touched. Quantitatively, this means that the coefficient of kinetic friction between the two layers is less than the coefficient between the fingertips and the second layer and less than the coefficient between the body part being touched and the first layer. Suitable liquid lubricants include mixtures of water and soap, glycerine, propylene glycol, polyoxyethylene (also known as polyethylene glycol), and silicone-based lubricants such as polydimethylsiloxane. The preferred liquid lubricant is ORGANOSILICONE L-45, a polydi-methylsiloxane which is a commercial product of Union Carbide Corporation, Danbury, Conn. For a nine-inch diameter mitt, about 10 to 30 ml of liquid lubricant are preferred.

Figure 3:
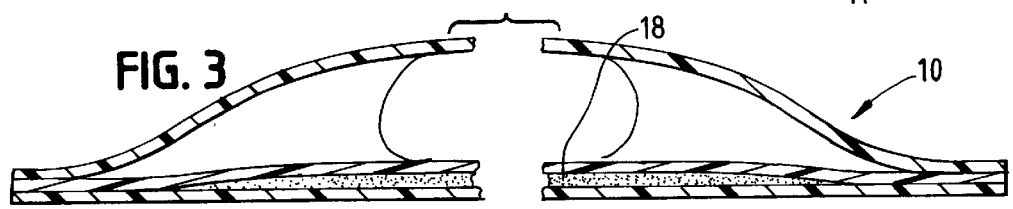
FIG. 3 is a cross-sectional view of a second embodiment of the touch enhancing mitt of this invention.

The second embodiment of the mitt shown in FIG. 3 contains a powdered lubricant 18. Like suitable liquid lubricants, suitable powdered lubricants have sufficient lubricity so that the top layer moves with the fingertips while the bottom layer remains stationary over the body part being touched. Suitable powdered lubricants must not only have sufficient lubricity, they must also be free of graininess that would interfere with the enhancement of the sense of touch. Graininess is believed to be a function of the size, shape, and hardness of the powder. Suitable powdered lubricants generally have an average particle size of less than about 15 to 20 microns. Preferred powdered lubricants preferably have an average particle size less than about 10 microns. The most preferred powdered lubricants include graphite, primary amides having the formula $R-O-NH_2$ where R is a saturated or unsaturated alkyl group having 10 to 30 carbon atoms, and blends thereof. These lubricants have high lubricities and adhere strongly to polyethylene and polyurethane. A preferred graphite is Extra Fine Graphite, a commercial product of Superior Graphite Co., Chicago, Ill. A preferred primary amide is erucamide, $C_{21}H_{41}-CO-NH_2$, a primary amide derived from rapeseed oil. The alkyl portion of the molecule contains one double bond. A highly preferred erucamide is CRODAMIDE ER, a commercial product of Croda Universal, Inc., Germantown, Tenn. The lubricant is present in an amount sufficient to fully coat the interior of the enclosure. For a nine-inch diameter mitt, about 0.1 to 2 grams of powdered lubricant are preferred.

Figure 4:
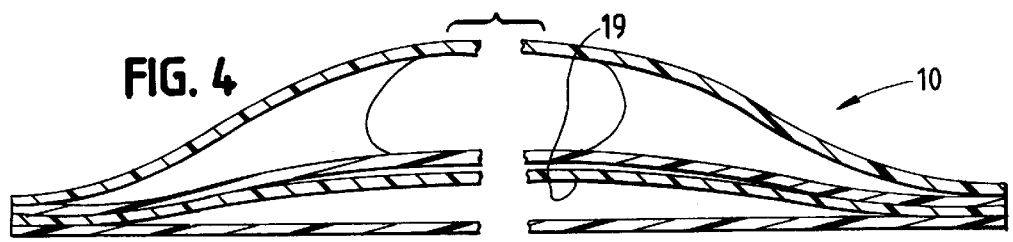
FIG. 4 is a cross-sectional view of a third embodiment of the touch enhancing mitt of this invention.

The third embodiment of the mitt shown in FIG. 4 contains an additional layer of material 19 between the first and second layers. This additional layer acts as a lubricant between the first and second layers. The material for the inner layer of the pad is generally different than the material for the outer layers of the pad. While the outer layer material is strong, thin, pliable, elastic, and smooth, the primary characteristics of the inner layer material are that it reduces friction and is thin. The inner layer material has a thickness of about 0.001 to 0.010 inches, preferably about 0.002 to 0.006 inches. The selection of the inner layer material is dependent upon the outer layer materials. In other words, different inner layer materials more effectively reduce the friction between different outer layer materials. Representative inner layer materials include certain polyesters, polyolefin copolymers, polyolefins, polychloroprene polymers, butadiene-styrene copolymers, butadiene-acrylonitrile copolymers, and polyurethane polymers. Preferred inner layer materials are polyesters and polyethylene copolymers. Most preferred inner layer materials include VILMED M1528 polyester and VILMED M1573FH cellulose polyester, commercial products of Freudenberg Faservliesstoffe KG of Weinheim, Germany, and SF-18 methyl acrylate/polyethylene copolymer, a commercial product of CT Film, Chippewa Falls, Wis.

4. Pocket Forming Layer

The third layer of material is secured to the second layer so as to form a pocket opening into which the hand of the user can be inserted. The third layer is made of a material which is strong enough to resist tearing or puncturing. The material is preferably pliable enough that it can fold over upon itself as the mitt is used. The third layer is not used for touch enhancement so properties such as elasticity, and smoothness are not essential. Suitable materials include synthetic and natural elastomeric sheets, such as those suitable for the touch enhancing first and second layers, as well as synthetic and natural fabrics. Manufacturing and inventory control are simplified if the same type of material is used for the third layer as is used for the touch enhancing first and second layers.

Figure 5:
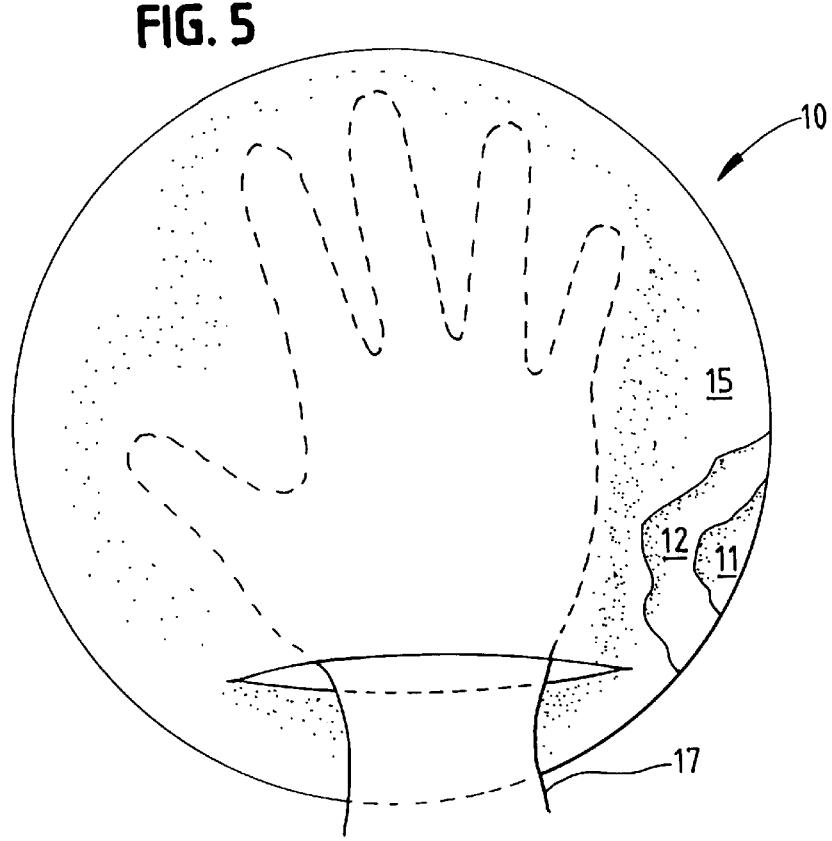
FIG. 5 is a perspective view of a fourth embodiment of the touch enhancing mitt of this invention.
Figure 6:
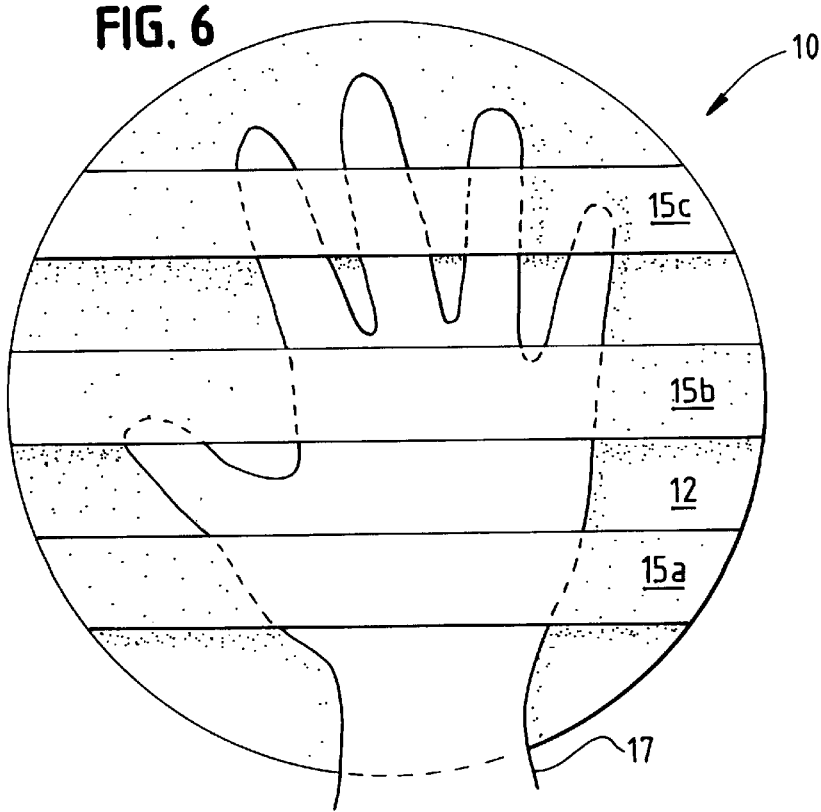
FIG. 6 is a perspective view of a fifth embodiment of the touch enhancing mitt of this invention.

The shape and size of the pocket forming third layer are such that it holds the hand in the mitt. In the preferred embodiment, the third layer is identical in shape to the first and second layers except for a missing arch-shaped portion where the hand is inserted. Other shapes are suitable. For example, in the embodiment shown in FIG. 5, the third layer is circular with a slit 20 in it for insertion of the hand. In the embodiment shown in FIG. 6, the third layer consists of strips 15a, 15b, and 15c that hold the hand in place.

5. Layer Attachment And Sealing

The way in which the layers of material are attached to each other and sealed varies from embodiment to embodiment. In the preferred embodiment, the enclosure is made of two layers of material that are heat sealed along their entire perimeter to contain the liquid lubricant. The third layer of material is also heat sealed along its perimeter. Heat sealing is preferred, but other sealing means are also suitable. For example, the use of adhesives is suitable with any lubricant while stitching, stapling, and the like are suitable for non-liquid lubricants.

In the second embodiment containing a powdered lubricant, the enclosure is sealed along some or all of its outside edge. The primary purpose of the sealing in this embodiment is to secure the two layers together. Sealing also helps to prevent the loss of any powdered lubricant. However, many of the powdered lubricants adhere so strongly to the inside surfaces of the enclosure that loss of lubricant is not a concern. Furthermore, the ease with which the top layer passes over the bottom layer is improved somewhat if the layers are not sealed along the entire outside edge.

If natural rubber latex is used for the enclosure, a single piece of latex is typically used because latex cannot be effectively heat sealed or glued. A preferred latex rubber enclosure has the general shape and appearance of a toy balloon with a single opening physically sealed to prevent the flow of material therethrough. Suitable physical seals include clamps, bands, and the like.

6. Size and Shape

The shape and size of the enclosure is not critical. The enclosure may be large or small depending upon the object to be touched and it may be round, square, or other shape as desired. While the enclosure can be approximately the same size as the hand, it is preferred that the enclosure be larger than the hand so there is some freedom of movement within the mitt. For breast examination, a round enclosure having a diameter of about nine inches is preferred because it fully covers and conforms to the shape of the breast.

7. Gas

For mitts that are completely sealed around their perimeter, it is desirable to include a volume of gas inside the enclosure. The presence of a small quantity of gas improves the ease with which the first and second layers pass over each other. The gas has substantial inertness towards the enclosure and is preferably air for ease of manufacture. The combined volumes of the lubricant and the gas permit the enclosure to be flattened with at least about 75 percent of the surface area of one side in contact with the other side. In the example of the nine-inch diameter pad, about 100 to 500 ml of gas are preferred. If the enclosure is not completely sealed, some air is always present between the two layers of the enclosure.

8. Use Of The Mitt

To use the mitt, the hand is placed into the pocket with the palm facing the first and second layers. The mitt is then placed onto the body part, or other object, to be touched. The fingertips are then used to examine the body part just as if the mitt were not present. The first layer of the mitt (the one in contact with the body part being touched) remains stationary while the second layer (the one in contact with the fingertips) moves with the fingertips. Optimal results are obtained when the fingertips are dry, i.e., free of any discernible amounts of liquids such as water, oils, or lotions. Liquids generally reduce the coefficient of kinetic friction between the fingertips and the top layer of material, which is undesirable. Liquids also appear to actually interfere with the reception of touch stimuli by the fingertips.

9. Theory Of Operation

While not wishing to be bound by theory, it is believed that at least five factors contribute to the touch enhancing properties of this mitt. First of all, the pad eliminates or masks certain touch stimuli such as temperature and texture and thereby improves the ability to detect the touch stimuli which enable shape and hardness to be determined. Second, the pad reduces friction between the user and the object being touched. This eases the movement of the fingertips across the object and helps prevent any tendency of the finger-tips to skip across a portion of the object.

Third, this method helps immobilize the object being touched. A very small object, protrusion, or indentation is detected most readily by passing the fingertips across it. If the object moves with the fingertips, it is more difficult to detect. For example, it is very difficult to feel a single human hair upon a hard, smooth surface. At least part of the difficulty is because the hair tends to stick to the fingers. When this method is used, the hair is immobilized and the fingertips can be moved back and forth across the hair, enabling it to be detected.

Fourth, the layers of material adhere to and follow the contours of objects so well that they, in effect, increase the size of the object for detection purposes. In the above example of human hair, the increase in the hair's diameter by several thousandths of an inch (which results when the two layers conform and adhere to the hair) creates a much larger protrusion for the fingertips to feel. Fifth, the use of the pad may actually increase the surface area of the fingertips in contact with the object.

I claim:

1. A mitt that enhances the sense of touch when worn on a hand of a user as an object is touched with the palm side of the fingertips, the mitt comprising:

(a) an enclosure of a first and a second layer of a pliable and elastic sheet material, the first and second layers of materials being sealed together along their perimeter to form the enclosure;

(b) a lubricant inside the enclosure in an amount great enough to fully coat the interior of the enclosure and yet small enough to permit the enclosure to be flattened with at least 75 percent of the surface area of one layer in contact with the other layer, the lubricant having sufficient lubricity that the coefficient of kinetic friction between the layers of the enclosure is less than the coefficient of kinetic friction between the fingertips and the enclosure and less than the coefficient of kinetic friction between the object being touched and the enclosure; and (c) a third layer of sheet material covering part or all of the second layer and attached to the second layer along part or all of the second layer's perimeter to form an opening between the second and third layers and to form a pocket into which the hand of the user can be inserted with the palm facing toward the second layer, wherein the first, second, and third layers have a wall thickness of about 0.005 to 0.015 inches, a modulus of elasticity at 200 percent elongation of less than about 4,000 psi, a tensile strength of greater than about 2,000 psi, and an ultimate elongation of greater than about 300 percent so that the layers are resistant to tearing or puncturing and are adopted to conform to the contours of the object being touched and to readily transmit touch stimuli.

2. The apparatus of claim 1 wherein the lubricant comprises a silicone-based lubricant.

3. The apparatus of claim 2 wherein the first, second, and third layers are made of the same material.

4. The apparatus of claim 3 wherein the mitt comprises first, second, and third layers of synthetic elastomer sheet heat fused together.

5. The apparatus of claim 4 wherein the first, second, and third layers comprise polyethylene sheet.

6. The apparatus of claim 4 wherein the first, second, and third layers comprise polyurethane sheet.

7. The apparatus of claim 1 wherein the lubricant comprises a powdered lubricant which is present in an amount great enough to fully coat the interior of the enclosure and yet small enough to permit the enclosure to be flattened with at least about 75 percent of the surface area of one wall in contact with the other wall.

8. The apparatus of claim 7 wherein the powdered lubricant comprises a primary amide having the formula R—CO—NH$_2$ where R is a saturated or unsaturated alkyl group having 10 to 30 carbon atoms.

9. The apparatus of claim 8 wherein the primary amide comprises erucamide.

10. The apparatus of claim 9 wherein the first, second, and third layers made of the same material.

11. The apparatus of claim 1 wherein the lubricant comprises a fourth, inner layer of material sandwiched between the first and second layers of material.

* * * * *